(12) United States Patent
Predick

(10) Patent No.: US 12,414,780 B2
(45) Date of Patent: Sep. 16, 2025

(54) VERTEBRAL ENDPLATE SHAVER WITH HEIGHT ADJUSTABLE BLADES

(71) Applicant: Life Spine, Inc., Huntley, IL (US)

(72) Inventor: Daniel P. Predick, Wheat Ridge, CO (US)

(73) Assignee: Life Spine, Inc., Huntley, IL (US)

( * ) Notice: Subject to any disclaimer, the term of this patent is extended or adjusted under 35 U.S.C. 154(b) by 393 days.

(21) Appl. No.: 17/991,658

(22) Filed: Nov. 21, 2022

(65) Prior Publication Data

US 2023/0157711 A1 May 25, 2023

Related U.S. Application Data

(60) Provisional application No. 63/315,638, filed on Mar. 2, 2022, provisional application No. 63/281,915, filed on Nov. 22, 2021.

(51) Int. Cl.
*A61B 17/16* (2006.01)
*A61B 17/00* (2006.01)
(Continued)

(52) U.S. Cl.
CPC *A61B 17/1671* (2013.01); *A61B 2017/00367* (2013.01); *A61B 2017/0042* (2013.01);
(Continued)

(58) Field of Classification Search
CPC ...... A61B 17/1671; A61B 2017/00367; A61B 2017/0042; A61B 2017/320008; A61B 2017/564
See application file for complete search history.

(56) References Cited

U.S. PATENT DOCUMENTS

| 2005/0277971 A1* | 12/2005 | Melkent ............. A61B 17/1671 |
| | | 606/180 |
| 2007/0162034 A1 | 7/2007 | Kostuik et al. |
| 2013/0325048 A1 | 12/2013 | Weiman |

FOREIGN PATENT DOCUMENTS

| WO | 2012016334 A1 | 2/2012 |
| WO | 2021041889 A1 | 3/2021 |

OTHER PUBLICATIONS

International Search Report and Written Opinion of the International Searching Authority, European Patent Office, Feb. 21, 2023, Munich, Germany.

* cited by examiner

*Primary Examiner* — Sameh R Boles
(74) *Attorney, Agent, or Firm* — Bruce J. Bowman

(57) ABSTRACT

A vertebral endplate preparation (decorticating) tool has height adjustable blades at a distal end of a shaft assembly for decorticating/shaving vertebral endplate material from spinal vertebrae, translates axial movement of a control rod o the shaft assembly of the vertebral endplate preparation tool with height adjustable blades into radial blade height change (extension and retraction) through a controller of a handle assembly. The blades may also be configured for collecting and removing shaved vertebral endplate material. The blades controllably move outward radially from the distal end of the shaft assembly and controllably move inward radially into the distal end of the shaft assembly upon manipulation of the controller. Radial blade extension and retraction from the distal end may be accomplished via mutual angled dovetail features of the blades and the distal end, or via pins of the distal end of the shaft assembly situated in angled slots of the blades.

5 Claims, 13 Drawing Sheets

(51) Int. Cl.
 *A61B 17/32* (2006.01)
 *A61B 17/56* (2006.01)
(52) U.S. Cl.
 CPC .............. *A61B 2017/320008* (2013.01); *A61B 2017/564* (2013.01)

VERTEBRAL ENDPLATE SHAVER WITH HEIGHT ADJUSTABLE BLADES

CROSS-REFERENCE TO RELATED APPLICATIONS

This U.S. non-provisional patent application claims the benefit of and/or priority under 35 U.S.C. § 119(e) to U.S. provisional patent application Ser. No. 63/281,915 filed November 22, 2021 titled "Expandable Vertebral Disc Micro Shaver" and U.S. provisional patent application Ser. No. 63/315,638 filed Mar. 2, 2022 titled "MIS Vertebral Endplate Shaver With Height Adjustable Blades," the entire contents of each of which are specifically incorporated herein by reference.

FIELD OF THE INVENTION

The present invention relates to instruments for spine procedures and, more particularly, to medical instruments for removing vertebral endplate material from a vertebra in a vertebral disc space of a spine.

BACKGROUND OF THE INVENTION

Many people contend with spine issues due to age, disease, trauma, congenital, and acquired complications and conditions. While some spine issues can be alleviated without surgery, other spine issues necessitate surgery. Spine surgery may entail removing vertebral disc material from between adjacent vertebrae. This can be accomplished using minimally invasive surgery, micro surgery, or the like. Such surgery reduces trauma by using surgical instruments that are introduced into the body via one or more small incisions. Certain of these medical instruments are introduced into the body via an access tube, endoscope, cannula or the like (collectively, cannula) that has been inserted into the body through a small incision and positioned accordingly. Other medical instruments can then be inserted into the cannula and controlled accordingly. Some medical instruments include a "built-in" cannula wherein the medical instrument with the cannula is inserted into an incision, positioned accordingly, and manipulated.

Various surgical spine procedures may be performed via a cannula (separate from or as part of the medical instrument). When an intervertebral spine implant is to be installed between adjacent vertebrae (i.e. in the vertebral disc space) it is necessary to properly prepare endplate surfaces of the adjacent vertebrae. Proper vertebral endplate surface preparation typically includes using a medical instrument with a cannula such as a vertebral endplate preparation instrument/tool (vertebral endplate shaver) to decorticate or shave the vertebral endplate surfaces to ensure adequate seating of the intervertebral spine implant. Typical vertebral endplate preparation tools have static blades (i.e. their blade(s) are fixed in height) that are inserted into a vertebral disc space and rotated to decorticate vertebral endplate surfaces of adjacent vertebrae. Because the blades are fixed in height a series of static vertebral endplate preparation tools each one having blades of a different radial height is therefore used to decorticate or shave the vertebral endplate surfaces. Such a series may be deemed a set of static vertebral endplate preparation tools.

Using static vertebral endplate preparation tools to properly decorticate vertebral endplate surfaces can increase the likelihood of problems since multiple static vertebral endplate preparation tools must be inserted into and removed from the cannula during the spine procedure. However, with a vertebral endplate preparation tool having height adjustable (dynamic) blades, a single medical instrument can be used to decorticate vertebral endplate surfaces. It is therefore preferable to use a vertebral endplate preparation tool having blades that can be easily varied in height.

Various vertebral endplate preparation tools with height adjustable blades have heretofore been devised. However, prior art vertebral endplate preparation tools with height adjustable blades suffer from several shortcomings such as, but not limited to, overall ease of use, ease of varying blade height, and not being conducive to use with a cannula.

It would therefore be desirable to have a vertebral endplate preparation tool with height adjustable (dynamic) blades that overcomes the deficiencies of prior art vertebral endplate preparation tools with height adjustable blades. The present vertebral endplate preparation tool with height adjustable (dynamic) blades addresses the above and more.

SUMMARY OF THE INVENTION

A medical instrument in the form of a vertebral endplate preparation tool with height adjustable (dynamic) blades for decorticating/shaving vertebral endplates during a spine procedure particularly, but not necessarily, using a cannula, has a head with at least one height adjustable blade for decorticating/shaving vertebral endplate material from a vertebra of a spine. The height adjustable blade(s) is/are configured to controllably move outward radially from the head and controllably move inward radially into the head upon manipulation of a controller of the vertebral endplate preparation tool with height adjustable instrument that is coupled to the head. The amount of outward radial movement of the blade(s) is controllable to set a height of the blade(s). With the blade(s) radially moved outward, they extend radially beyond a diameter of the head and an associated cannula. Rotation of the head via a handle of the vertebral endplate preparation tool with height adjustable rotates the blade(s) to allow decorticating of the vertebral endplates.

In one form, the present vertebral endplate preparation tool with height adjustable blades has a handle, a controller operably connected to the handle, a control shaft defining a distal control shaft end and a proximal control shaft end that is operably connected to the controller for controlled manipulation of the control shaft, and a head on the distal control shaft end having first and second blades for decorticating or shaving vertebral endplates of vertebrae of a spine. The first and second blades controllably move outward radially (expand) from the head, and controllably move inward radially (collapse) into the head upon manipulation of the controller. The vertebral endplate preparation tool with height adjustable blades may include a cannula with the control shaft disposed within. Movement of the handle operates the controller to manipulate the control shaft to axially extend the head from a cannula, controllably expand the first and second blades radially outward to a desired height from the head beyond a diameter of the cannula after the head has been extended from the cannula, and contract the first and second blades into the head when vertebral endplate decorticating/shaving is finished.

In one form, each blade has a concave portion for allowing shaved vertebral endplate material to collect therein. In one form, cutouts or windows in a lower portion of the blade(s) aid in allowing vertebral endplate material to be collected, then removed. When rotated, the blades(s) provide an almost 180° collection sweep outside of a longitudinal plane (axis) of the associated cannula.

The head has a nose and a rear or base that each slidingly hold an end of each blade for radial expansion/contraction of each blade from the head. The moving connection between the nose and an end of the blades is preferably, but not necessarily, via angled dovetail configurations. The moving connection between the base and another end of the blades is also preferably, but not necessarily, via angled dovetail configurations.

Once the head is external of the cannula, axial movement in one direction of a component of the control shaft that is connected to a nose of the head, pulls the nose axially towards the base of the head to provide axial compression. Axial compression of the nose towards the base axially compresses against the movable blades to slide them radially outward from the nose and base to expand the blades from the head. Axial movement of the control shaft in an axially opposite direction allows retraction of the blades into the head, through release of axial pressure.

In another form, the dynamic vertebral endplate preparation tool has height adjustable blades at a distal end of a shaft assembly for decorticating/shaving vertebral endplate material from vertebrae of a spine, translates axial movement of a control rod of a shaft assembly into radial blade height change (radial blade height extension or retraction) through a controller of a handle assembly of the dynamic vertebral endplate preparation tool. The blades controllably move outward radially (extend) from the distal end of the shaft assembly and controllably move inward radially (retract) into the distal end of the shaft assembly upon manipulation of the controller in a head of the dynamic vertebral endplate preparation tool that is connected to the shaft assembly.

Once the blades are expanded, they extend radially beyond a diameter of an associated cannula. Rotation of the blades turn the blades to provide decorticating/shaving of vertebral endplate material. The blades may be configured to also collect and removal of shaven vertebral endplate material.

Radial extension and retraction of the blades from the distal end of the shaft assembly is accomplished in one form via mutual angled dovetail features of the blades and the distal end whereby axial force against the blades (compression) via the control rod effects radially outward movement (extension) of the blades via the mutual angled dovetail features between the blades and the distal end (a first axial direction). Reverse axial movement of the control rod releases axial pressure (force) against the blades to effect radially inward movement (retraction) of the blades. In one form, the distal end has angled dovetail slots or channels that receive angled dovetail ends or flanges of the blades (a second axial direction opposite the first axial direction). In a particular form, the distal end has front angled dovetail slots/channels and rear angled dovetail slots/channels that receive respectfully a front dovetail end or flange and a rear dovetail end or flange of each blade.

Radial extension and retraction of the blades from the distal end is accomplished in one form via pins of the distal end situated in angled slots of the blades whereby axial translation of the pins against the angled slots of the blades in one direction effects radially outward movement (extension) of the blades, while axial translation of the pins against the angled slots of the blades in the reverse direction effects radially inward movement (retraction) of the blades. In a particular form, each blade has two angled slots while the control rod has two pins, one pin for each of the two angled slots of the blades. The two angled slots of each blade are situated skewed relative to each other.

In use, manipulation of the controller of the handle provides extension of the blades radially outward from the distal end beyond a diameter of the cannula after the distal end is clear of the cannula, and retract the blades into the distal end when use of the dynamic vertebral endplate preparation tool is finished.

Each blade may include a trough for collecting, and then removing, the shaven vertebral endplate material. In a particular form, cutouts or windows in a lower portion of the blade(s) aid in collection of shaved vertebral endplate material during use. When rotated, the blades(s) provide an almost 180° collection sweep outside of a longitudinal plane (axis) of the associated cannula.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The present invention and its features will be better understood by reference to the accompanying drawings, wherein.

Figure 1:
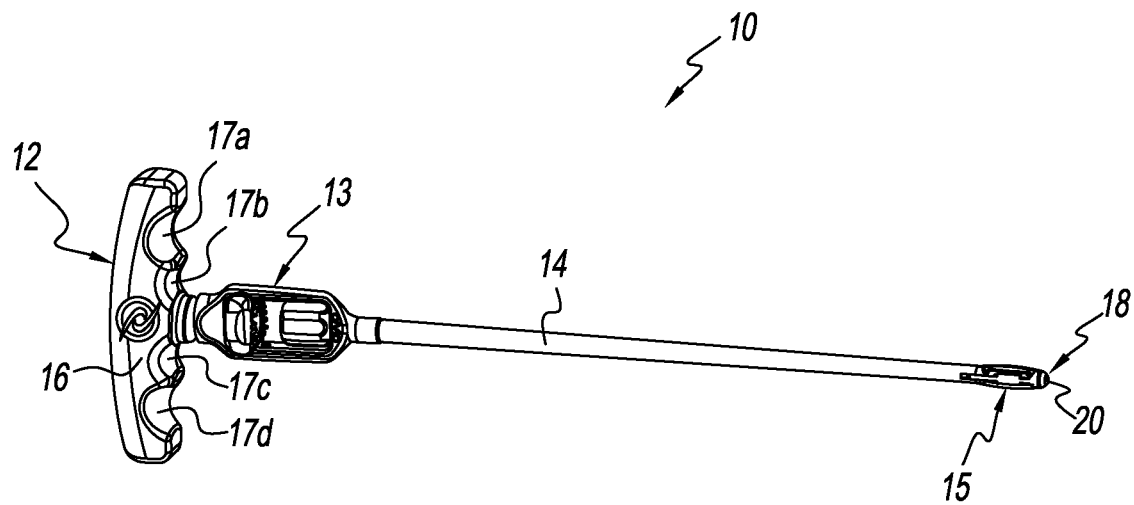
FIG. 1 is a view of an exemplary vertebral endplate preparation tool with height adjustable blades for decorticating/shaving vertebra endplate material from vertebrae of a spine fashioned in accordance with the present principles.

For the purposes of promoting an understanding of the principles of the invention reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

DETAILED DESCRIPTION OF THE INVENTION

Referring to FIGS. 1-14, there is shown an exemplary medical instrument, generally designated 10 for decorticating or shaving vertebral endplate material from vertebrae of a spine, and optionally collecting and removing vertebral endplate material (not shown) from a vertebra (not shown) of a spine (not shown) during a surgical spine procedure, particularly, but not necessarily, using a cannula. The medical instrument 10 may be considered a vertebral endplate preparation tool with height adjustable (dynamic) blades and is made from one or more surgical grade materials. The vertebral endplate preparation tool with height adjustable blades 10 has a head 15 with blades 22, 24 designed to shave, collect, and remove vertebral disc material from a vertebral disc. The blades or shavers 22, 24 are movably retained in the head 15 such that each blade 22, 24 is able to extend or spread outward radially from the head, and retract or collapse inward radially from the head when actuated by the vertebral endplate preparation tool with height adjustable blades 10. The radial spread of the blades 22, 24 is beyond the diameter of an associated cannula 80, such as, but not necessarily, to the height of a vertebral disc space. Axial compression of the nose 20 to the base 46 of the head 15 that slidingly retain curved ends 50, 51 of the blade 22 and curved ends 48, 49 of the blade 24 provides radial expansion of the blades 22, 24, while relieving axial compression provides radial contraction of the blades 22, 24.

FIG. 1 depicts an overall view of the vertebral endplate preparation tool with height adjustable blades 10. The vertebral endplate preparation tool with height adjustable blades 10 has a handle 12, a controller 13 operably coupled to the handle 12, a control shaft 14 operably coupled to the controller 14, and a head 15 operably coupled to a distal end 18 of the control shaft 14. The handle 12 is characterized by a gently curved body 16 sized to accommodate a hand (not shown) and includes several indentions 17a, 17b, 17c, 17d each configured to accommodate a finger. Other configurations may be used.

Figure 2:
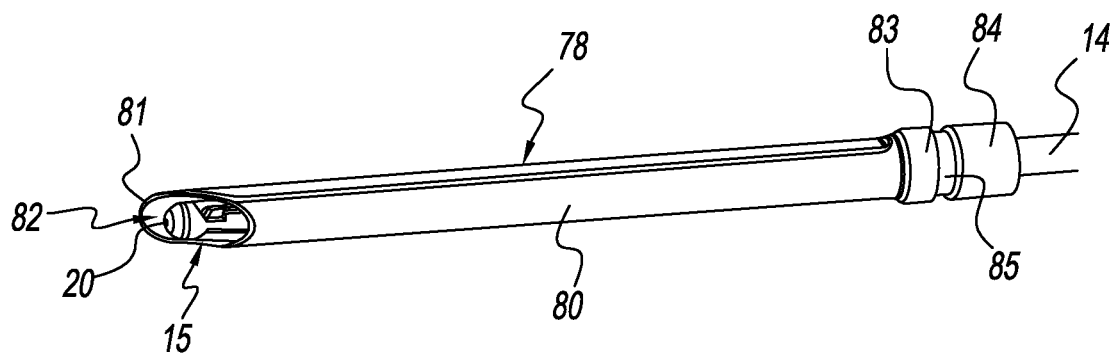
FIG. 2 is an enlarged view of a middle to distal portion of the exemplary vertebral endplate preparation tool with height adjustable blades of FIG. 1, depicting a bladed head thereof ready for extension and deployment from a cannula.

FIG. 2 depicts a cannula construction 78 defined by a hollow longitudinal cannula 80 having a distal angled end 81, an inner longitudinal bore 82, and a proximal end 83 that is shown receiving a secondary cannula 85 having a receiving end 84. The control shaft 14 is shown extended into the cannula construction 78 with the head 15 of the medical instrument 10 in a pre or post-deployment/expansion position at the distal angled end 81 of the cannula 80. Through the use of telescoping cannula construction 78, overall length of the cannula may be adjusted as desired. Other configurations may be used.

Figure 3:
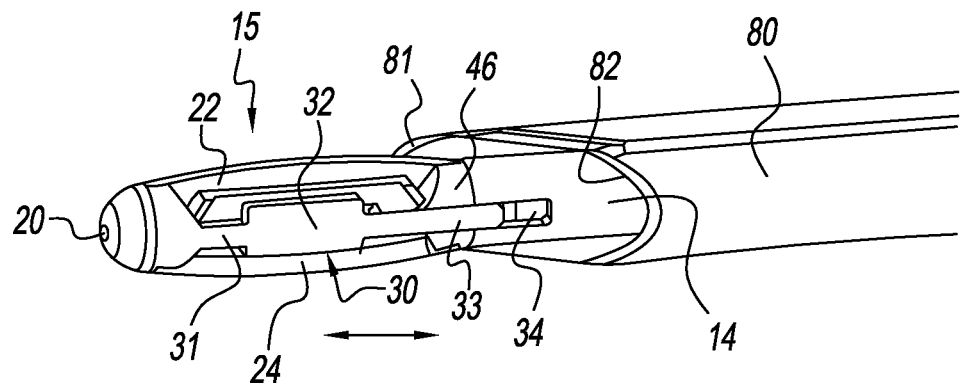
FIG. 3 is an enlarged view of a distal end of the exemplary vertebral endplate preparation tool with height adjustable blades of FIG. 1 with the bladed head shown in an extended but un-deployed position.
Figure 4:
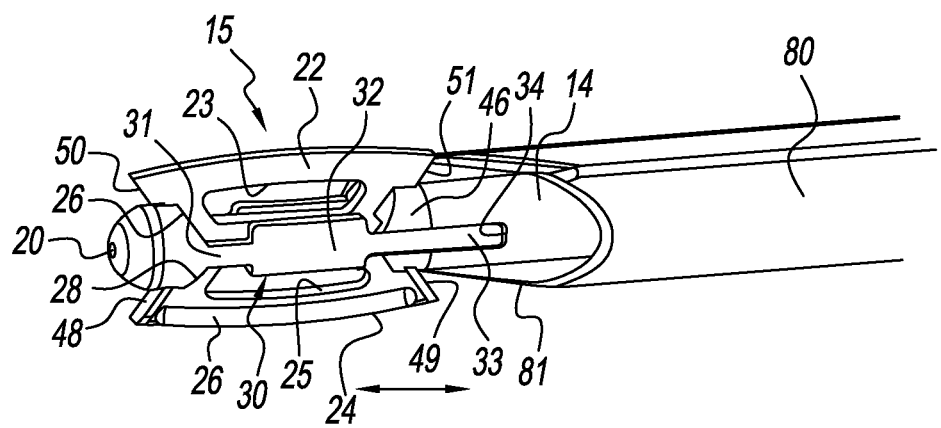
FIG. 4 is an enlarged view the distal end of the exemplary vertebral endplate preparation tool with height adjustable blades of FIG. 1 with the bladed head shown in an extended and deployed position.
Figure 5:
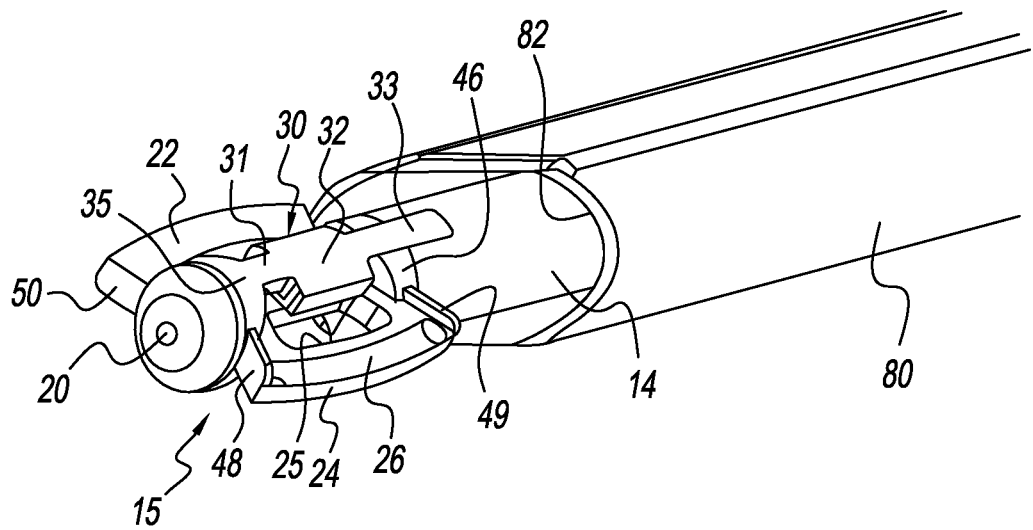
FIG. 5 is an enlarged view of the distal end of the exemplary vertebral endplate preparation tool with height adjustable blades of FIG. 1 with the bladed head shown in an extended, deployed and rotated position.
Figure 6:
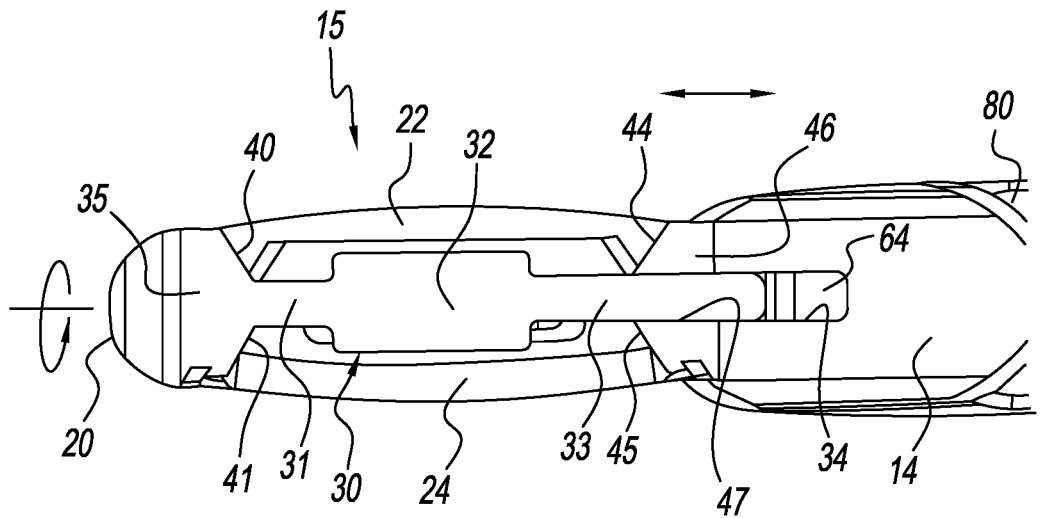
FIG. 6 is an enlarged side view of the distal end of the exemplary vertebral endplate preparation tool with height adjustable blades of FIG. 1 with the bladed head shown in an extended but un-deployed position.

FIGS. 3-7 depict various views of the head 15 of the present vertebral endplate preparation tool with height adjustable blades 10 as it emerges from the end 81 of bore 82 of the cannula 80. The overall shape of the head 15 is cylindrical which therefore defines arcs or arcuate portions about the circumference and/or the axial length of the overall cylindrical shape of the head. The head 15 has a nose 20 at a distal end of the head 15, and a base 46 at a proximal end of the head 15. The nose 20 is shaped generally as a flattened arch, but other shapes may be used. The base 46 is fixed to the control shaft 14, which itself axially moves within the cannula 80, as regulated by the controller 13 via the handle 12. As seen in FIGS. 3, 4, and 6, for example, the base 46 is situated at and fixed to the distal end of the control shaft 14. A first blade or shaver 22 is situated axially between the nose 20 and the base 46 along an axial length of the outer diameter of the cylindrical shape of the head 15, while a second blade or shaver 24 is situated axially between the nose 20 and the base 46 along another axial length of the outer diameter of the cylindrical shape of the head 15 and generally diametrically opposite the first blade 22, the nomenclature first and second being arbitrary. The first blade 22 is held between the nose 20 and the base 46 such that the first blade 22 can move radially outward (expand) and radially inward (collapse) with respect to the head 15. The first blade 22 further includes a concavity, groove, cutout, depression, scoop, or the like 26 that extends along the curved longitudinal edge of the first blade 22 which is configured to receive and/or collect shaved vertebral disc material. A window 23 is provided in the first blade 22 that aids in collection of shaved vertebral disc material. The second blade 24 is also held between the nose 20 and the base 46 such that the second blade 24 can move radially outward (expand) and radially inward (collapse) with respect to the head 15. The second blade 24 further includes a concavity, groove, cutout, depression, scoop, or the like (not seen) that extends along the curved longitudinal edge of the second blade 24, which is configured to receive and/or collect shaved vertebral disc material in like manner and form as scoop 26. A window 25 is provided in the second blade 24 that aids in collection of shaved vertebral disc material. Axial motion is controlled through the control shaft 14 from the controller 13 through the handle 14.

The nose 20 has a collar or skirt 35 (collectively, collar) that extends axially from the proximal end of the nose 20 a distance towards the base 46. One side of the collar 35 has a first, preferably, but not necessarily, angled slot 40 that is configured to movably or slidingly receive a first angled side 50 of the blade 22. The first slot 40 of the nose 20 and the first angled side 50 of the blade 22 are preferably, but not necessarily, formed between them as a dovetail joint. Another side of the collar 35 has a second, preferably, but not necessarily, angled slot 41 that is configured to movably or slidingly receive a first angled side 48 of the second blade 24. The second slot 41 of the nose 20 and the first angled side 48 of the second blade 24 are preferably, but not necessarily, formed between them as a dovetail joint.

The base 46 has a first, preferably, but not necessarily, angled slot 44 that is configured to movably or slidingly receive a second angled side 51 of the blade 22. The first slot 44 of the base 46 and the second angled side 51 of the blade 22 are preferably, but not necessarily, formed between them as a dual angled dovetail joint/channels. Another side of the base 46 has a second, preferably, but not necessarily, angled slot 45 that is configured to movably or slidingly receive a second angled side 49 of the second blade 24. The second slot 44 of the base 46 and the second angled side 49 of the second blade 24 are preferably, but not necessarily, formed between them as a dual angled dovetail joint/channels. Through axial compression and relief of axial pressure of the nose 20 axially towards the base 46 and axially away from the base 46, the first and second blades 22, 24 are caused to move relative to the nose 20 and the base 46 because of the slanted ends of the blades and the slots of the nose and the base. Axial pressure of the nose 20 towards the base 46 causes the first and second blades 22, 24 to slide up, out and along (spread out or expand from the head 15) the dovetail configurations between the ends of the blades and the slots of the nose and base, while relief of axial pressure of the nose 20 away from the base 46 causes the first and second blades 22, 24 to slide down, in and along (collapse or compress into the head 15) the dovetail configurations between the ends of the blade and the slots of the nose and the base.

The head 15 also has an actuator 30 that extends from the collar 35 of the nose 20 towards the base 46. The actuator 30 provides a connection for controlling axial movement of the nose 20 relative to the base 46 for controlling blade expansion/contraction. While not seen in the figures, the head 15 may include a second actuator situated opposite to the actuator 30 that would mimic the actuator 30. The actuator 30 includes a first arm 31 that extends axially from the end of the collar 35 and is connected to one side of a first plate 32. A second arm 33 extends axially from a second side of the first plate 32 towards and through a channel 47 in the side of the base 46. The second arm 33 further extends axially through and is retained in a groove 34 formed in an outside surface of the control shaft 14. As signified by the double-headed arrow in FIGS. 3, 4 and 6, the actuator 30 is able to axially translate relative to the base 46 and control shaft 14. This is accomplished by a translational shaft 64 of the control shaft 14 that is connected to the actuator 30 and which can axially move relative to the body of the control shaft 14 through the controller 13. When the translational shaft 64 is axially translated in one direction, the actuator 30 axially pulls against the nose 20 to squeeze (axially translate) it towards the base 46 thereby pushing out (expanding) the first and second blades 22, 24. Axial translation of the translational shaft 64 in the opposite axial direction pushes the nose 20 axially away from the base 64 to collapse the first and second blades 22, 24 into the head 15.

Figure 7:
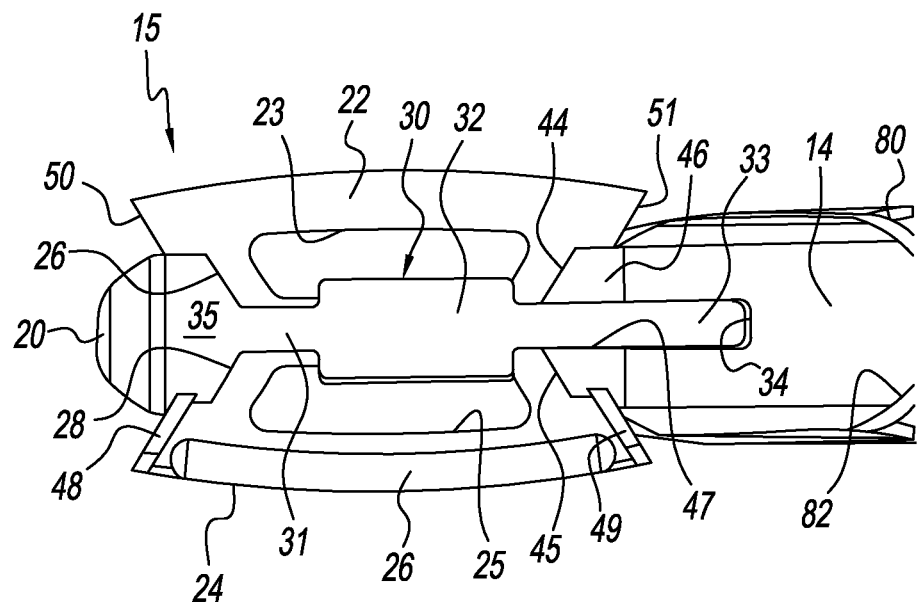
FIG. 7 is an enlarged side view of the distal end of the exemplary vertebral endplate preparation tool with height adjustable blades of FIG. 1 with the bladed head in an extended and deployed position.

FIGS. 3-5 depict expansion of the blades 22, 24 from the head 15 as the head 15 emerges (is axially translated from) the cannula 80. FIG. 6 depicts a side view of the head 15 with the blades 22, 24 un-expanded, while FIG. 7 depicts a side view of the head 15 with the blades 22, 24 expanded. FIGS. 10-14 depict various views of the head 15 with the blade 22, 24 expanded and un-expanded showing the control shaft 14 and the translational shaft 64 relative to the actuator 30 and blades 22, 24.

Figure 8:
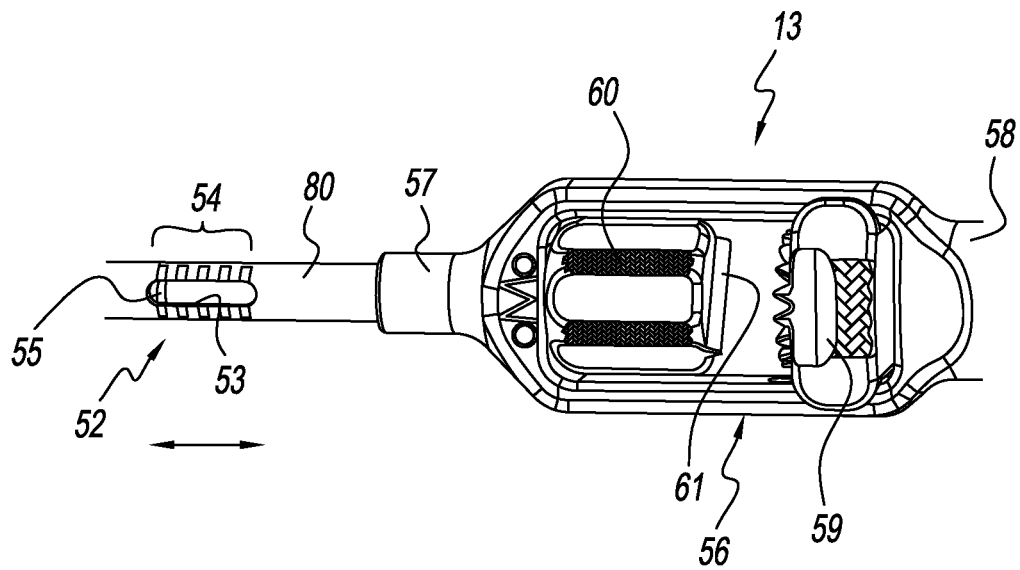
FIG. 8 is an enlarged view of a controller of the exemplary vertebral endplate preparation tool with height adjustable blades of FIG. 1.
Figure 9:
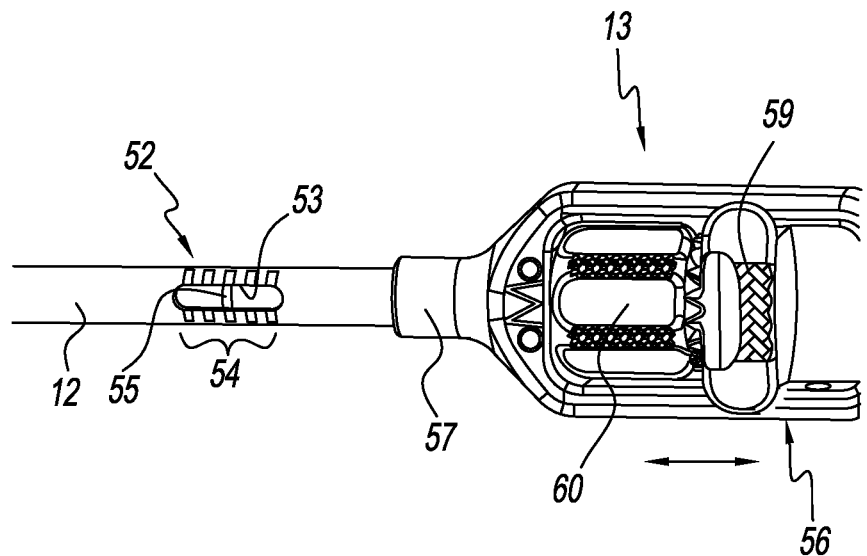
FIG. 9 is another enlarged view of the controller of the exemplary vertebral endplate preparation tool with height adjustable blades of FIG. 1.
Figure 10:
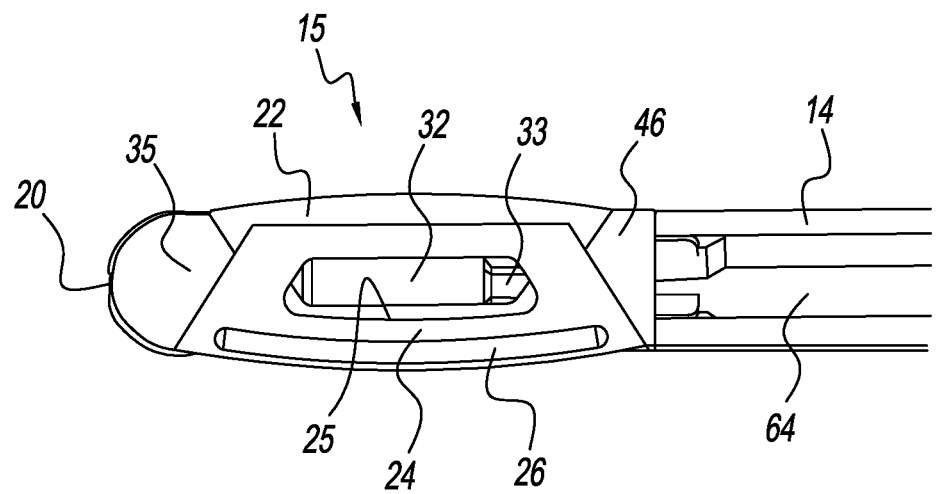
FIG. 10 is an enlarged side view of the bladed head and distal end portion of the exemplary vertebral endplate preparation tool with height adjustable blades of FIG. 1 with the bladed head in an un-deployed position.
Figure 11:
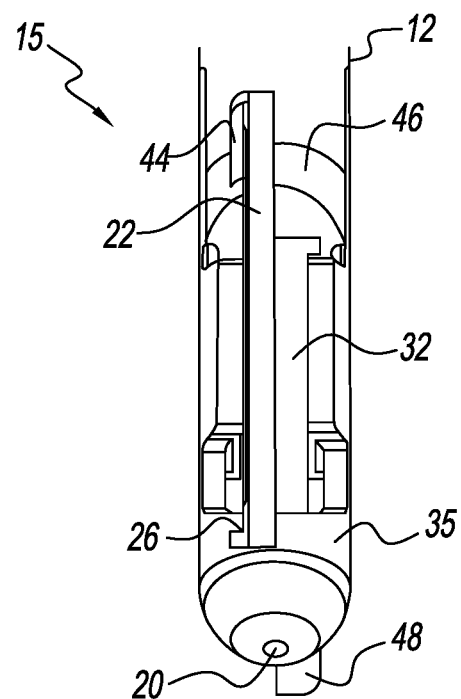
FIG. 11 is an enlarged view of the bladed head and distal end portion of the exemplary vertebral endplate preparation tool with height adjustable blades of FIG. 1 with the bladed head and distal end portion in an un-deployed position.
Figure 12:
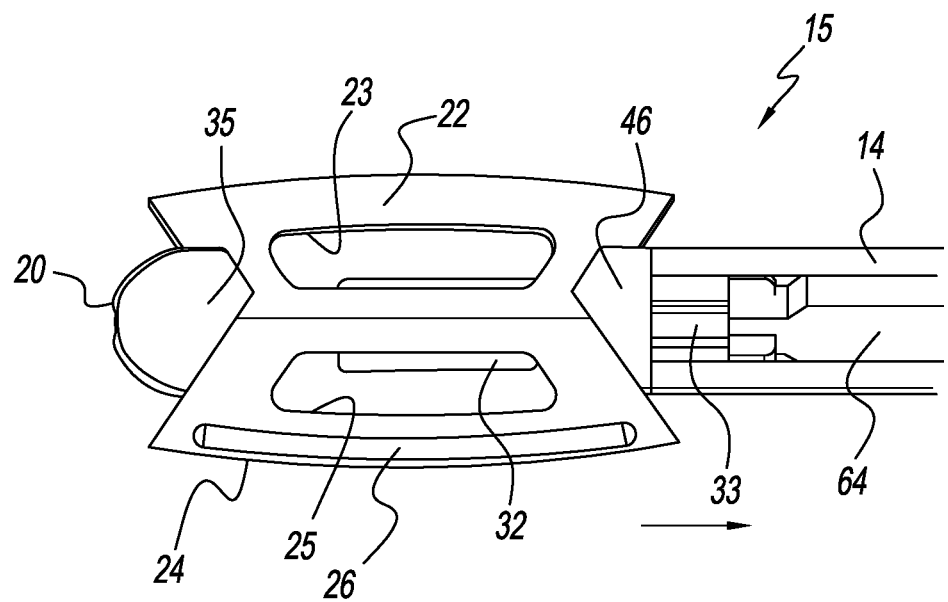
FIG. 12 is an enlarged side view of the bladed head and distal end portion of the exemplary vertebral endplate preparation tool with height adjustable blades of FIG. 1 with the bladed head and distal end portion in a deployed position.
Figure 13:
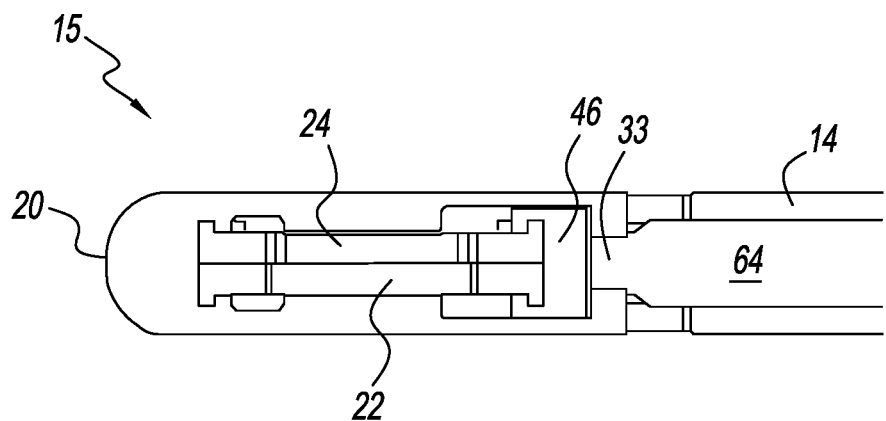
FIG. 13 is an enlarged side view of the bladed head and distal end portion of the exemplary vertebral endplate preparation tool with height adjustable blades of FIG. 1 with the bladed head and distal end portion in an un-deployed position.
Figure 14:
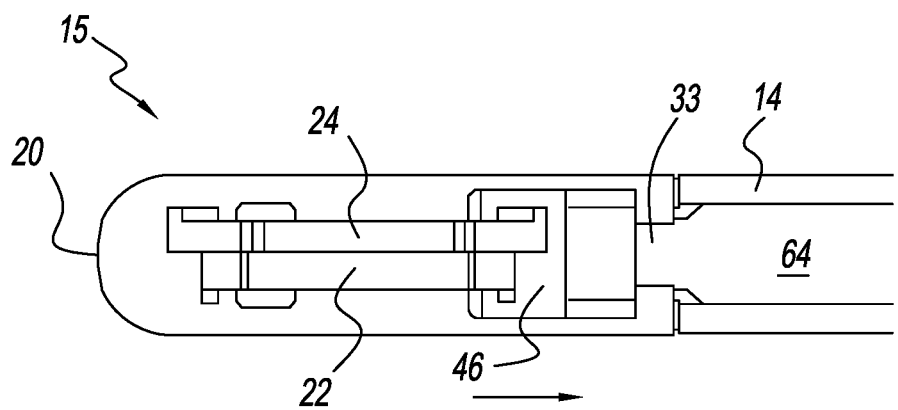
FIG. 14 is another enlarged side view of the bladed head and distal end portion of the exemplary vertebral endplate preparation tool with height adjustable blades of FIG. 1 with the bladed head and distal end portion in an un-deployed position.

FIGS. 8-9 depict two views of the controller 13. The controller 13 has a body 56 connected to the handle 12 via a neck 58. The handle 12 is operably coupled to a control knob 60 for axially moving the control shaft 14 within the cannula 80. A toothed tab 59 is slidingly retained by the body 13 and when slid into a locked position (FIG. 9) where the teeth thereof meet end 61 of the control knob 60. Thus, control knob 60 is locked in orientation via sliding the lock tab 59 down from the open position (shown in FIG. 8) to a locked position (shown in FIG. 9) which will prevent (e.g., lock) the blades 22, 24 from collapsing into the head 15 when in use.

The cannula 80 extends from the neck 57 of the body 56 of the controller 13 and may include a head position indicator 52 for indicating status of the head 15. The indicator 52 includes an opening or window 53 formed in the cannula 80 with demarcations 54 about the opening 53 to indicate axial position of the head 15 relative to the opening 81 of the cannula 80. The control shaft 14 has a mark 55 that will move axially within the opening 53 with axial movement of the control shaft 14, as signified by the double-headed arrow in FIG. 8.

Referring to FIGS. 15-23, there is shown another form of a vertebral endplate preparation tool with height adjustable blades generally designated 110 for decorticating/shaving vertebral endplate material from vertebrae (not shown) of a spine (not shown) during a surgical procedure. The medical instrument 110 may also be configured and used for collecting and removing the shaved vertebral endplate material. The medical instrument 110 is preferably, but not necessarily, used with a cannula or endoscope during a minimally invasive or micro invasive spine procedure. The vertebral endplate preparation tool with height adjustable blades 110 is made from one or more surgical grade materials. In general, the vertebral endplate preparation tool with height adjustable blades 110 has a proximal end/end assembly 111 with a handle 112 that is connected to a proximal end of a controller 113 via a neck 118, a shaft assembly 114 connected at a proximal end thereof to a distal end of the controller 113 via a collar 115, and a head 122 at a distal end 120 of the shaft assembly 114, the head 122 having a nose 121 and a blade assemblage/assembly 133 having first and second blades 136, 137 designed to decorticate or shave vertebral endplate material from a vertebra (not shown), the nomenclature first and second being arbitrary here and throughout if not specifically indicated otherwise. The vertebral endplate preparation tool with height adjustable blades 1110 may also be configured to collect and remove the shaved vertebral endplate material and is so configured as shown. The first and second blades 136, 137 are movably retained in the head 122 such that each blade 136, 137 is able to extend or spread outward radially from the head 122, and retract or collapse inward radially from the head 122 when actuated by the vertebral endplate preparation tool with height adjustable blades 1110. The radial spread of the first and second blades 136, 137 is beyond the diameter of an associated cannula, access tube, endoscope or the like, such as, but not necessarily, to the height of a vertebral disc space (not shown), such that the medical instrument 1110 may decorticate or shave vertebral endplate material from adjacent vertebra within the disc space if desired, rather than each vertebral endplate of adjacent vertebrae separately.

Figure 16:
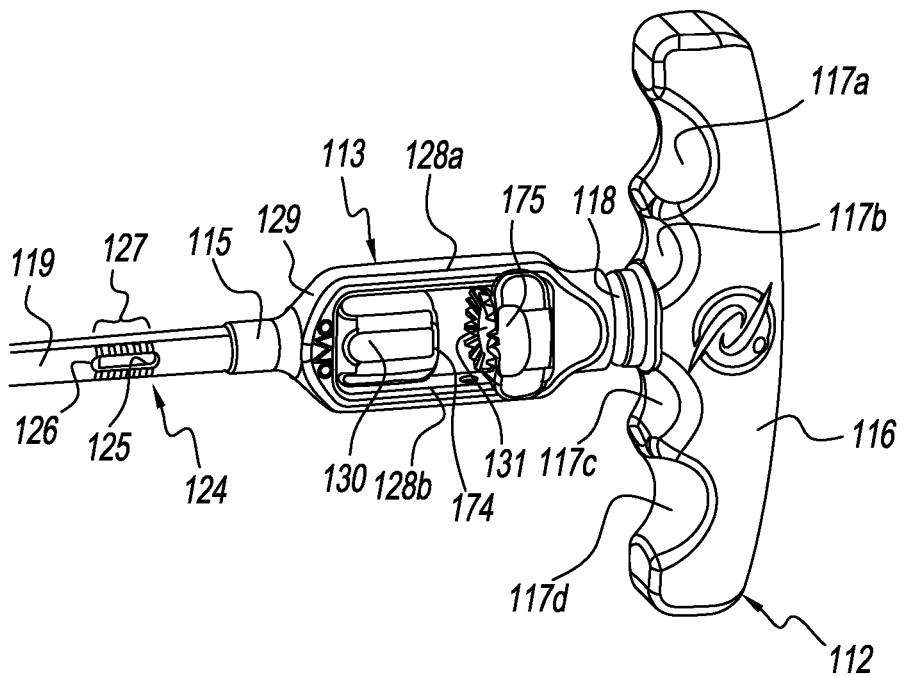
FIG. 16 is an enlarged view of a proximal end of the exemplary vertebral endplate preparation tool with height adjustable blades of FIG. 15, particularly showing the handle assembly.
Figure 17:
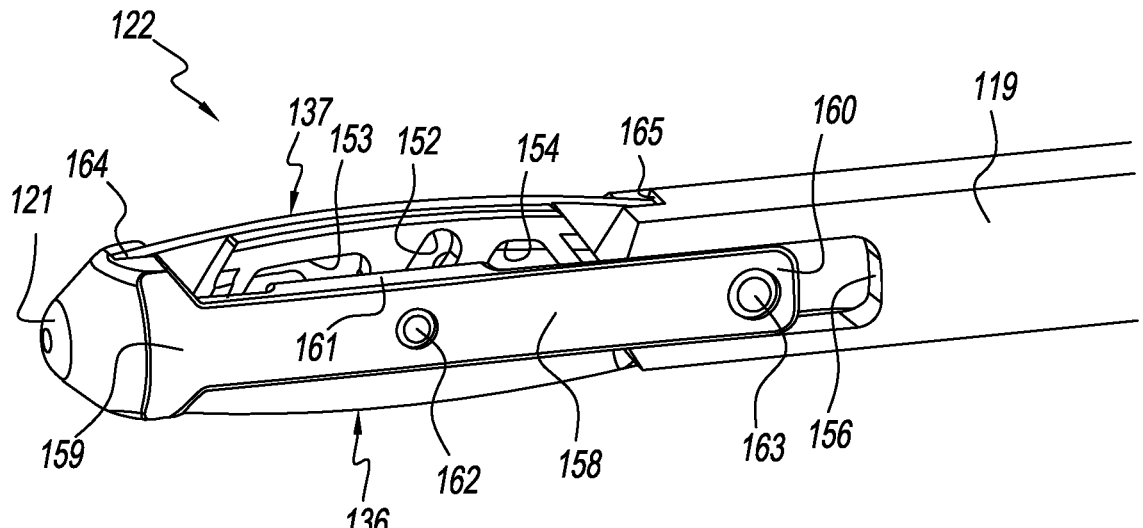
FIG. 17 is an enlarged view of the distal end of the exemplary vertebral endplate preparation tool with height adjustable blades of FIG. 15 with the blades shown retracted.
Figure 18:
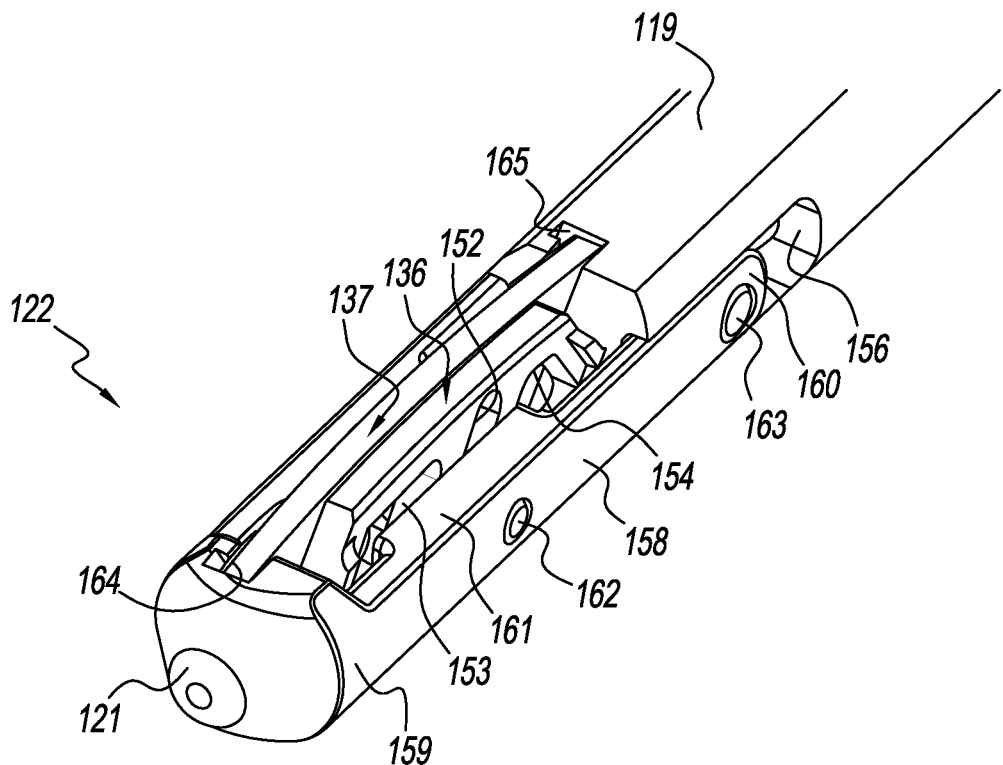
FIG. 18 is another enlarged view the distal end of the exemplary vertebral endplate preparation tool with height adjustable blades of FIG. 15 with the blades shown retracted.
Figure 19:
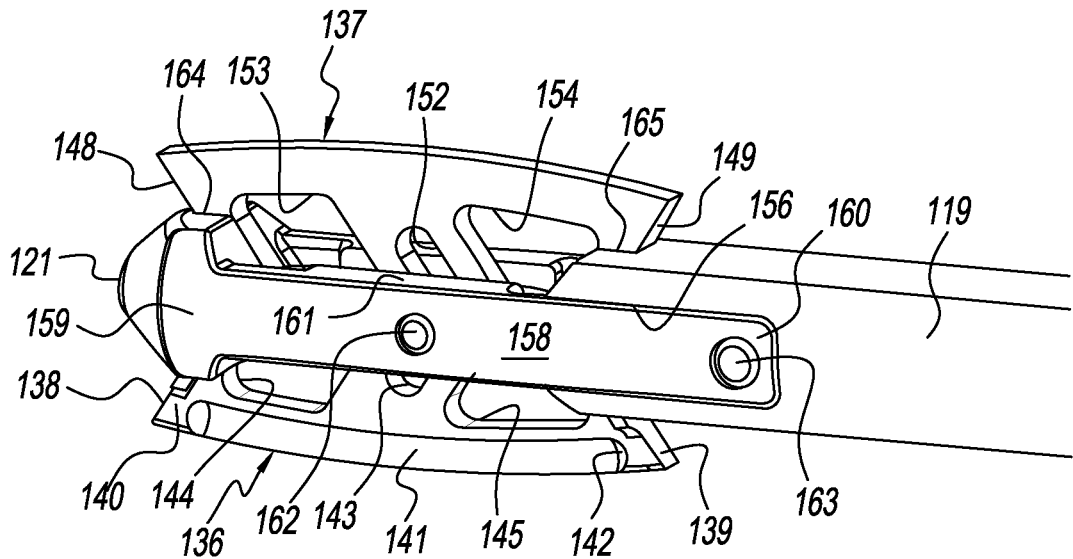
FIG. 19 is an enlarged generally side view of the distal end of the exemplary with height adjustable blades vertebral endplate preparation tool of FIG. 15 with the blades shown extended.
Figure 20:
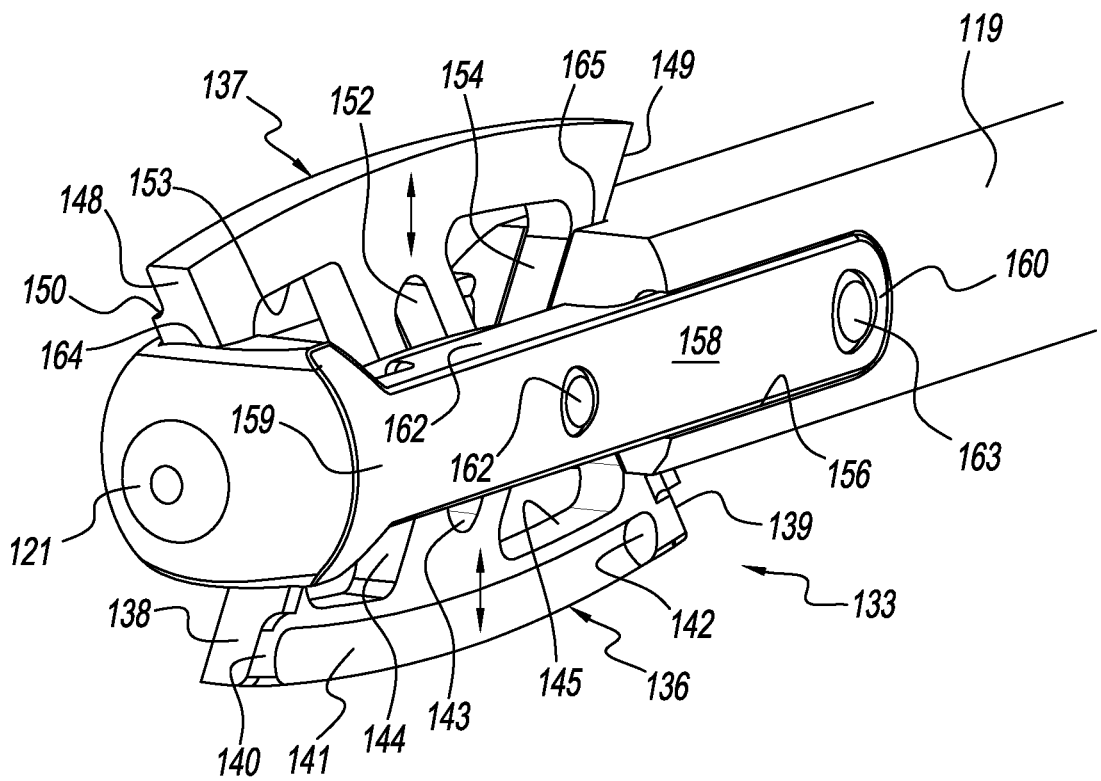
FIG. 20 is an enlarged front side view of the distal end of the exemplary vertebral endplate preparation tool with height adjustable blades of FIG. 15 with the blades shown extended.
Figure 21:
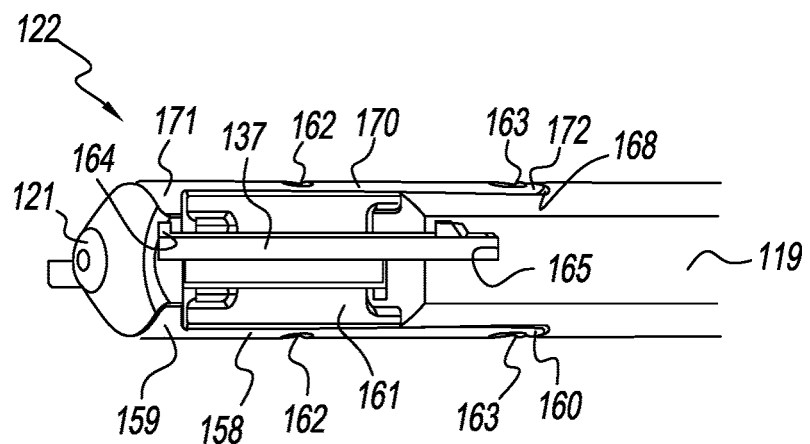
FIG. 21 is a top view of the distal end of the exemplary vertebral endplate preparation tool with height adjustable blades of FIG. 15 with the blades shown retracted.

Referring to FIG. 16, the handle 112 is characterized by a gently curved body 116 sized to accommodate a hand (not shown) and includes several indentions 117a, 117b, 117c, 117d each configured to accommodate a finger. Other configurations may be used. The controller 113 has a frame defined by upper and lower frame members 128a, 128b that project from the neck 118 of the handle 112. The upper and lower frame members 128a, 128b are connected to a front frame member 129 that connects to the collar 115. The controller 113 has a rotatable control knob 130 that adjusts the extension and contraction of the first and second blades 136, 137 through the handle 112 that is operably coupled to the control knob 160 for axially moving the control shaft 114 within the cannula 180. A toothed tab 175 is slidingly retained by the controller 113. In FIG. 16, the toothed tab 175 is in an unlocked position axially away from the rotatable control knob 160 such that the toothed tab 175 is not engaged with the rotatable control knob 160. When the toothed tab 175 is axially slid into a locked position (not shown) where the teeth thereof meet the toothed end 174 of the rotatable control knob 160, rotation of the handle 112 rotates the toothed tab 175 which rotates the rotatable control knob 160 to effect blade extension and retraction through the shaft assembly 114.

The shaft assembly 114 includes a generally hollow, longitudinal tube 119 having upper and lower flats along its longitudinal length and an internal control rod (not seen) that extends at a proximal end thereof from the rotatable control knob 160 to and operably connected with the blade assemblage 133 of the head 122 at a distal. The proximal end of the internal control rod is externally threaded. The rotatable control knob 160 has an internally threaded bore (not seen) that receives the externally threaded proximal end of the internal control rod of the shaft assembly 114. Rotation of the rotatable control knob 160 axially moves the internal control rod of the shaft assembly 114, the direction of axial movement of the internal control rod depending on the rotational direction of the rotatable control knob 160 through threaded engagement. As explained further below, axial movement of the internal control rod effects extension and retraction of the first and second blades 136, 137 from the head 122. The longitudinal tube 119 includes a blade height indicator 124 that provides a visual indication of blade height from the head 122. The height indicator 124 has an opening or window 125 formed in the longitudinal tube 119 with demarcations 126 about the opening 125 to indicate height position of the first and second blades 136, 137 from the head 122. The internal control rod 114 has a marker 126 that will move axially within the opening 125 with axial movement of the internal control rod.

FIGS. 17-21 depict various views of the head 122 and blade assemblage 133 of the present vertebral endplate preparation tool with height adjustable blades 110. The overall shape of the head 122 is generally cylindrical. The head 122 has a nose 121 at a distal end thereof, with a first surface 159 on a first lateral side, and a second surface 171 on a second lateral side. The first lateral surface 159 has a first arm 158 extending axially to the distal end of the longitudinal tube 119 with a first rear tail 160 received in a first axial slot 156 of the distal end of the longitudinal tube 119. The second lateral surface 171 has a second arm 170 extending axially to the distal end of the longitudinal tube 119 with a second rear tail 172 received in a second axial slot 168 of the distal end of the longitudinal tube 119, the first and second arms 158, 170 and the first and second rear tails 160, 172 being preferably, but not necessarily, opposite one another. The first and second arms 158, 170 and thus the nose 121 of the head 122 is longitudinally axially movable relative to the longitudinal tube 119, since the internal control rod of the shaft assembly 114 is attached thereto. Axial movement of the internal control rod towards the controller 113 pulls the nose 121 and arms 158, 170 to compress against the first and second blades 136, 137 thereby effecting blade extension through mutual dovetail features of the first and second blades 136, 137 and the distal end 122 along with slanted first and second channels 143, 152 of the first and second blades 136, 137 respectively, wherein the amount of axial movement determines radial height (extension) of the first and second blades 136, 137. Axial movement of the internal control rod of the shaft assembly 114 away from the controller 113 pushes the nose 121 and arms 158, 170 releases compression against the first and second blades 136, 137 to effect retraction of the first and second blades 136, 137.

The first blade 136 is situated axially between the nose 121 and the distal end of the longitudinal tube 119 of the shaft assembly 114. The first blade 136 is generally trapezoidal in overall shape with a gently curved outer longitudinal edge. As best discerned in FIGS. 19 and 20, the first blade 136 has a first slanted front 138 with at least a generally dovetail configuration and a first slanted rear 139 with at least a generally dovetail configuration. The gently curved outer longitudinal edge of the first blade 136 has a groove or channel 141 that extends between a first front end 140 and a first rear end 142 that is configured to receive and/or collect shaved vertebral endplate material. The groove 141 is on one side of the gently curved outer longitudinal edge of the first blade 136, while the opposite side of the gently curved outer longitudinal edge does not have a groove. As such, the first blade 136 is configured to be rotated in one direction (here, a clockwise direction) in order to shave vertebral endplate material from a vertebra (not shown). A first front cutout 144 and a first rear cutout 145 is provided in the first blade 136 that aid in collection of shaved vertebral endplate material. Situated between the first front cutout 144 and the first rear cutout 145 is a first angled slot 143. As best discerned in FIGS. 22 and 23, the first angled slot 143 is slanted from a distal position to the proximal direction. The first angled slot 143 is sized to receive a pin 162 that is held between and extends from the first arm 158 to the second arm 170. A first spacer 161 is provided between the first arm 158 and the first blade 136.

The second blade 137 is situated axially between the nose 121 and the distal end of the longitudinal tube of the shaft assembly 114. The second blade 137 is generally trapezoidal in overall shape with a gently curved outer longitudinal edge. As best discerned in FIGS. 19 and 20, the second blade 137 has a second slanted front 148 with at least a generally dovetail configuration and a second slanted rear 149 with at least a generally dovetail configuration. The gently curved outer longitudinal edge of the second blade 137 has a groove or channel (not seen) that extends between a second front end (not seen) similar to the first front end 140 of the first blade 136, and a second rear end (not seen) similar to the first rear end 142 of the first blade 136, that is configured to receive and/or collect shaved vertebral endplate material. The groove (not seen) is on one side of the gently curved outer longitudinal edge of the second blade 137, while the opposite side of the gently curved outer longitudinal edge does not have a groove. The groove (not seen) of the second blade 137 is on the side of the second blade 137 such that rotation in the same direction as the first blade 136 (here, a clockwise direction) provides shaving of vertebral endplate material from a vertebra (not shown). A second front cutout 153 and a second rear cutout 154 is provided in the second blade 137 that aid in collection of shaved vertebral endplate material. Situated between the second front cutout 153 and the second rear cutout 154 is a second angled slot 152. The second angled slot 152 is slanted from a distal position to the proximal direction in like manner to the first angled slot 143. The second angled slot 152 is sized to receive the pin 162 that is held between and extends from the first arm 158 to the second arm 170. A second spacer 173 is provided between the first arm 158 and the second blade 137.

The proximal end of the nose 121 has a first angled lower slot 166 that is configured as a dovetail slot to movably or slidingly receive the first angled front 138 of the first blade 136, whereby the first lower angled slot 166 and the first angled front 138 together define a dovetail joint. Other manners of connection may be used and are contemplated. The distal end of the longitudinal tube 119 has a second angled lower slot 167 that is configured as dovetail slot to movably or slidingly receive the first angled rear 139 of the first blade 136, whereby the second angled lower slot 167 and the first angled rear 139 together define a dovetail joint. Other manners of connection may be used and are contemplated. The slant of the first angled lower slot 166/first angled front 138 of the first blade 136 pair dovetail joint, and the slant of the second angled lower slot 167/first angled rear 139 of the first blade 36 pair dovetail joint are opposite one another, whereby axial compression against the first angled front 138 and the first angled rear 139 of the first blade 136 causes, at least in part, the first blade 136 to extend radially outward from the distal end 122. The pin 162 is connected to the distal end of the internal control rod. As the pin 162 is pulled axially towards the proximal end/end assembly 111, the first angled slot 143 of the first blade 136 rides against the pin 162 during extension. Reverse axial movement of the internal control rod pushes the pin 162 against the first angled slot 143 such that the first blade 136 is retracted. The amount of axial movement in the proximal direction determines the amount of blade extension.

The proximal end of the nose 121 further has a first angled upper slot 164 that is configured as a dovetail slot to movably or slidingly receive the second angled front 148 of the second blade 137, whereby the first angled upper slot 164 and the second angled front 148 together define a dovetail joint. Other manners of connection may be used and are contemplated. The distal end of the longitudinal tube 119 has a second angled upper slot 165 that is configured as dovetail slot to movably or slidingly receive the second angled rear 149 of the second blade 137, whereby the second angled upper slot 165 and the second angled rear 149 together define a dovetail joint. Other manners of connection may be used and are contemplated. The slant of the first angled upper slot 164/second angled front 148 of the second blade 137 pair dovetail joint, and the slant of the second angled upper slot 165/second angled rear 149 of the second blade 137 pair dovetail joint are opposite one another, whereby axial compression against the angled ends 148/149 of the second blade 137 causes, at least in part, the second blade 137 to extend radially outward from the distal end 122. The pin 162 is connected to the distal end of the internal control rod. As the pin 162 is pulled axially towards the proximal end/end assembly 111, the second angled slot 152 of the second blade 137 rides against the pin 162 during extension. Reverse axial movement of the internal control rod pushes the pin 162 against the second angled slot 152 such that the second blade 137 is retracted. The amount of axial movement in the proximal direction determines the amount of blade extension.

Figure 22:
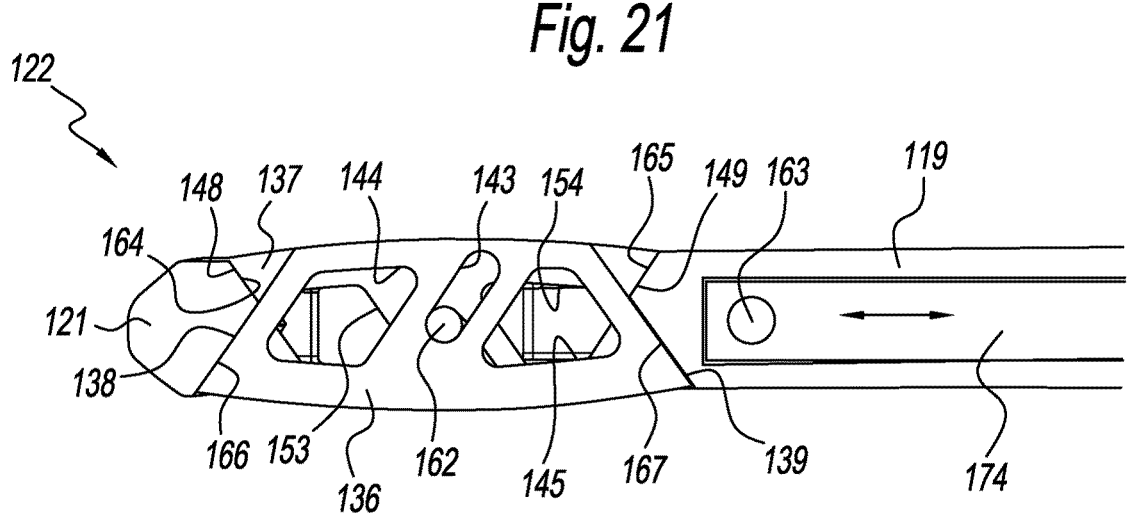
FIG. 22 is an enlarged side sectional view of the distal end of the exemplary vertebral endplate preparation tool with height adjustable blades of FIG. 15 with the blades shown retracted.
Figure 23:
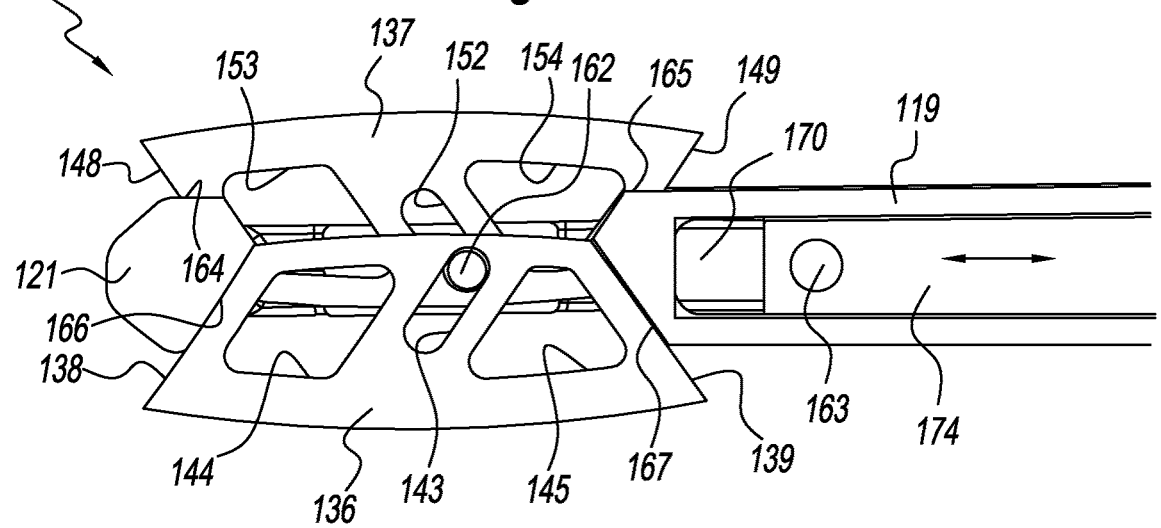
FIG. 23 is another enlarged side sectional view of the distal end of the exemplary vertebral endplate preparation tool of with height adjustable blades FIG. 15 with the blades shown extended.

FIGS. 22 and 23 show the extension of the first and second blades 136, 137 from the distal end 122, with one lateral side removed for clarity. In FIG. 22, the first and second blades 136, 137 are fully retracted. This is the position of the blades when the distal end 122 is inserted through an access tube (not shown). In FIG. 23, the first and second blades 136, 137 are fully extended. As the internal control rod is caused to axially move into the controller 113, the pin 162, being connected to the internal control rod, pulls the pin 162 and the nose 121 axially towards the controller 113. This causes the first and second blades 136, 137 to extend. The amount of extension is controlled by the controller 113, and visually indicated by the indicator 124 on the longitudinal tube 119 of the shaft assembly 114. Axial motion is signified by the double-headed arrow.

In operation, the distal end or shaving head 122 of the vertebral endplate preparation tool with height adjustable (dynamic) blades 110 is inserted down an access tube. Once clear of the distal end of the access tube, the decorticating/shaving head 122 is inserted into the vertebral disc space. The blades are extended by rotation of the rotatable control knob 130 via the handle 112 to a particular radial height necessary for the particular disc space. Rotation of the blades then effects shaving of vertebral endplate material.

Figure 15:
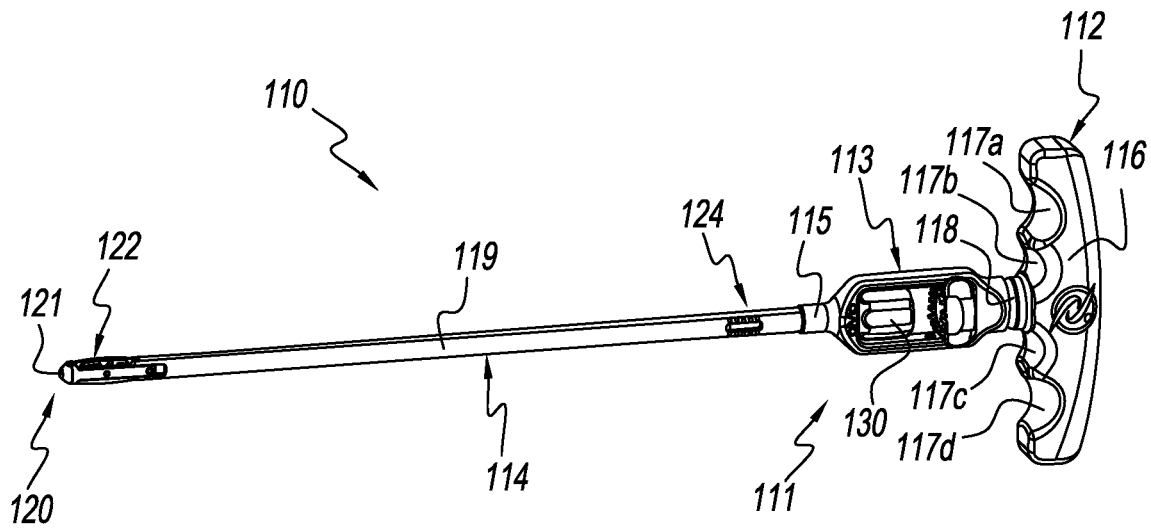
FIG. 15 is a view of another exemplary vertebral endplate preparation tool with height adjustable blades for decorticating/shaving vertebra endplate material from vertebrae of a spine fashioned in accordance with the present principles.
Figure 24:
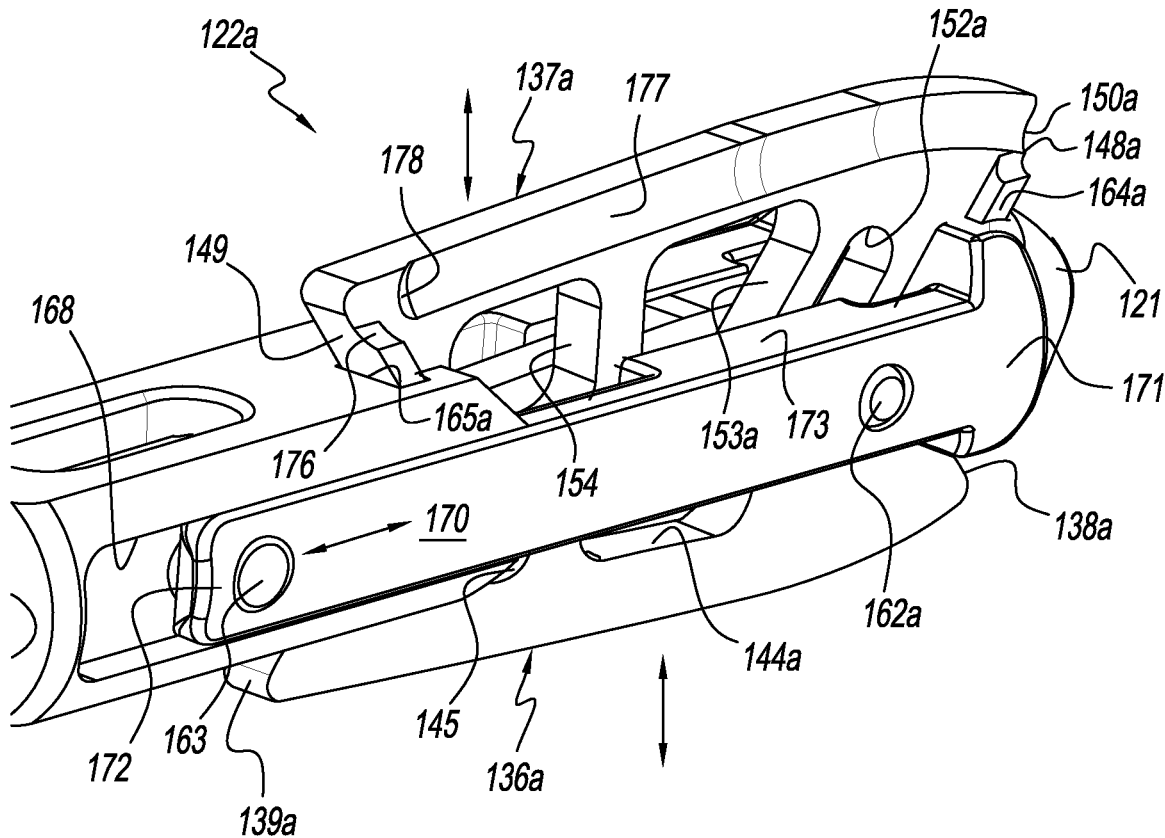
FIG. 24 is an enlarged view of a distal end of a further exemplary form of a vertebral endplate preparation tool with height adjustable blades for decorticating/shaving vertebral endplate material from vertebrae of a spine fashioned in accordance with the present principles with the blades thereof shown extended.

Referring to FIG. 24, there is depicted another form of a distal end/decorticating head 122 for the vertebral endplate preparation tool with height adjustable (dynamic) blades 110 dynamic shaver 110 of FIG. 15 designated 122*a*. The addition of the designation "a" after a callout number indicates an element or component that is different in some manner than the element or component of the vertebral endplate preparation tool with height adjustable blades 110 of FIGS. 15-23. All other elements or components without the additional designation of "a", or are not shown in FIG. 24, are the same in form and function as the vertebral endplate preparation tool with height adjustable (dynamic) blades 110 of FIGS. 15-23. Essentially, the shaving or decorticating head 122*a* has dovetail joints between the nose 121, the distal end of the internal control rod of the shaft assembly 114, and the first and second blades 136*a*, 137*a* of the shaving/decorticating head 122*a* with a different profile than the dovetail joints between the nose 121, the distal end of the internal control rod of the shaft assembly 114, and the first and second blades 136, 137 of the vertebral endplate preparation tool with height adjustable blades 110. Thus, the first angled lower slot 166*a*, the second angled lower slot 167*a*, the first angled front 138*a*, and the first angled rear 139*a* form a dovetail joint that allows the ramped surfaces between them (which force extension) includes a side profile that allows the height of the first blade 136*a* to be controllably decreased when operated in the opposite direction (blade retraction direction). As well, the first angled upper slot 148*a*, the second angled upper slot 149*a*, the second angled front 148*a*, and the second angled rear 149*a* form a dovetail joint that allows the ramped surfaces between them (which force extension) includes a side profile that allows the height of the second blade 137*a* to be controllably decreased when operated in the opposite direction (blade retraction direction).

Additionally, the first blade 136*a* has a pin slot 152*a* situated distally, and the second blade 137*a* has a pin slot (not seen in FIG. 24) also situated distally. The pin 162*a* of the first and second lateral arms 158, 170 is further situated distally. The first blade 136*a* has a middle opening 144*a*. The second blade 137*a* also has a middle opening 153*a*. Extension and retraction of the first and second blades 136*a*, 137*a* operates in the same manner as the vertebral endplate preparation tool with height adjustable blades 110.

Figure 25:
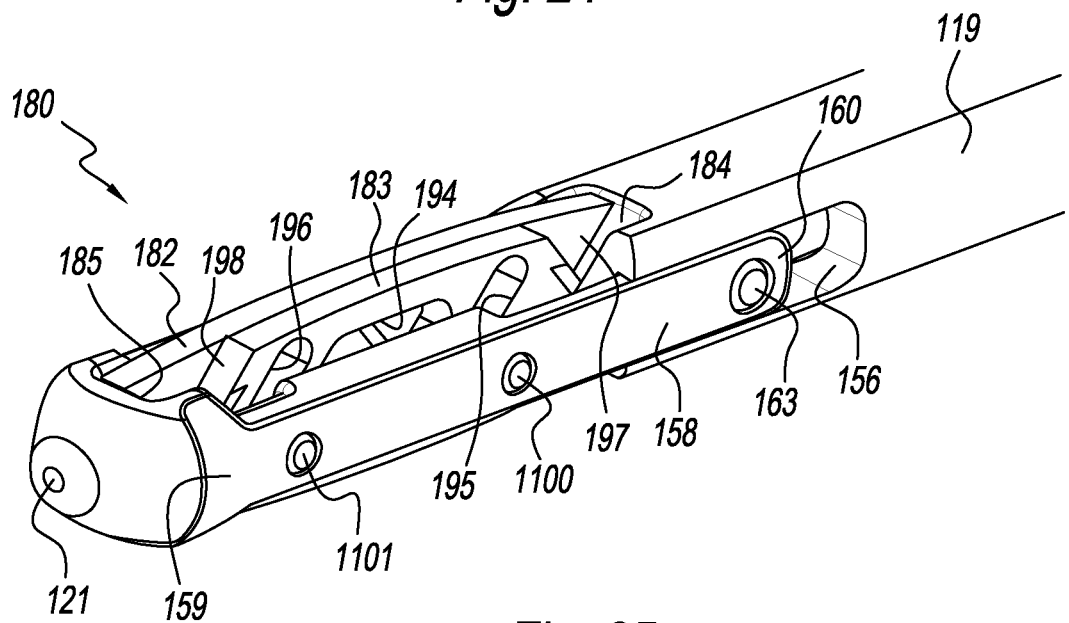
FIG. 25 is an enlarged view of a distal end of a still further exemplary form of a vertebral endplate preparation tool with height adjustable blades for decorticating/shaving vertebra endplate material from vertebrae of a spine fashioned in accordance with the present principles with blades of the distal end shown retracted.
Figure 26:
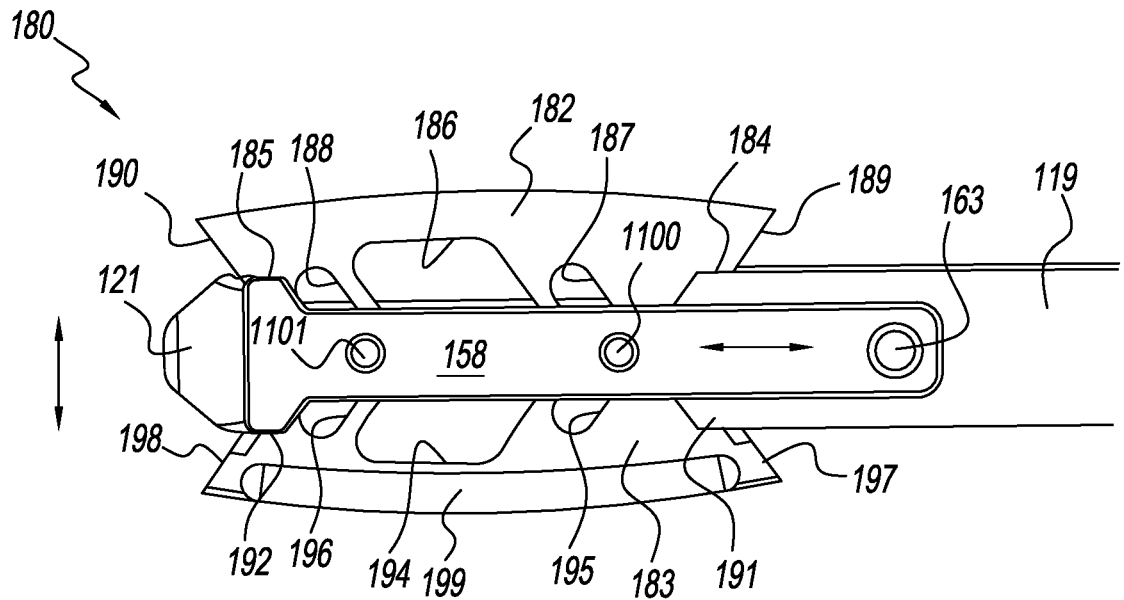
FIG. 26 is an enlarged side view of the distal end of the exemplary vertebral endplate preparation tool with height adjustable blades of FIG. 25 with the blades shown extended.
Figure 27:
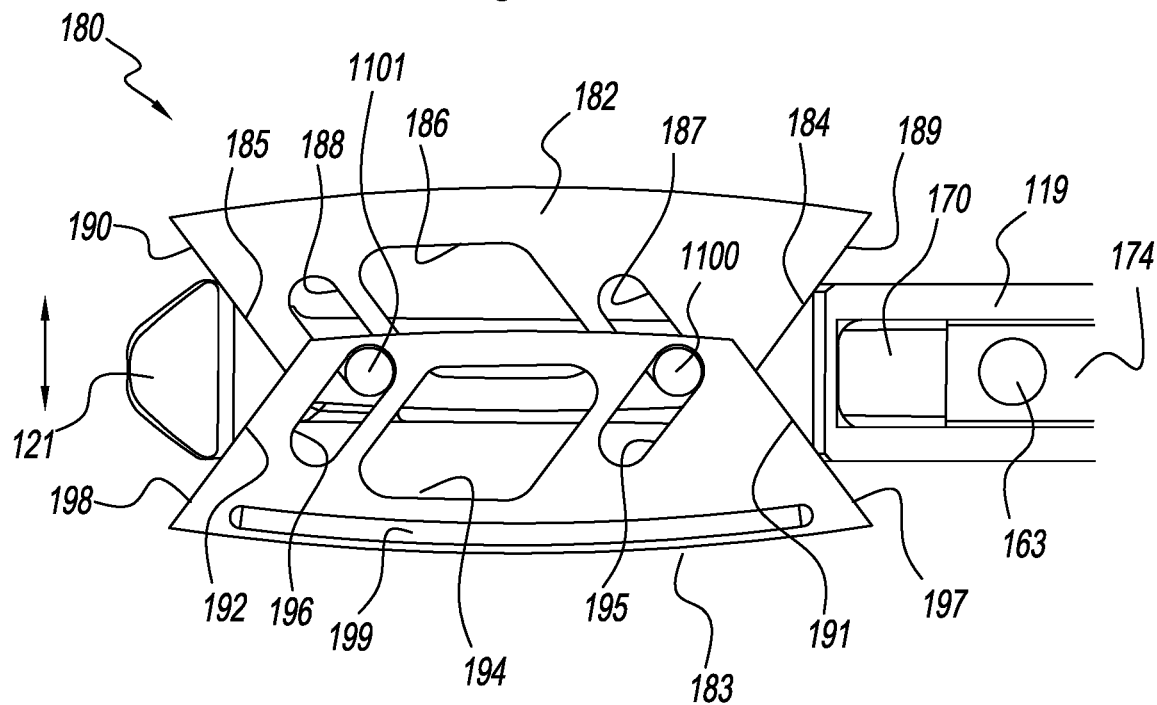
FIG. 27 is an enlarged side sectional view of the distal end of the exemplary vertebral endplate preparation tool with height adjustable blades of FIG. 25 with the blades shown extended.

Referring to FIGS. 25-27, there is depicted a further form of a vertebral endplate preparation tool with height adjustable (dynamic) blades 110 having a different distal end/shaving/decorticating head designated 180. The vertebral endplate preparation tool with height adjustable (dynamic) blades 110 of FIGS. 25-27 is different from the vertebral endplate preparation tool with height adjustable (dynamic) blades 110 of FIGS. 15-24 and the variation of the shaving head 22*a* of FIG. 24 because of the manner of how the shaving/decorticating head 80 operates, and thus configured. The shaving head 80 uses pins and slanted slots to effect extension and retraction rather than, or in addition to, dovetail joints. Other than the shaving head 80, the vertebral endplate preparation tool with height adjustable blades 110 of FIGS. 25-27 has, at least generally, the same elements, components, and functionality as the vertebral endplate preparation tool with height adjustable blades 110 of FIGS. 15-24, including the nose 121, the first and second lateral arms 158, 170 that extend from the nose 121 to the slots 156 and 168, respectively of the longitudinal tube 119, and connection pin 163.

The first blade 182 of the shaving head 180 has a first slanted rear 189 and a first slanted front 190, a central opening 186, a first angled rear slot 187, and a first angled front slot 188. The distal end of the longitudinal tube 119 has a first upper slanted channel 184 that receives the first slanted rear 189 of the first blade 182, while the proximal end of the nose 121 has a second upper slanted channel 185 that receives the first slanted front 190 of the first blade 182. A proximal guide pin 1100 extends from and through the first and second arms 158, 170 and the first angled rear slot 187 of the first blade 182. A distal guide pin 1101 extends from and through the first and second arms 158, 170 and the first angled front slot 188 of the first blade 182. The slant of the first angled front slot 188 and the slant of the first angled rear slot 187 are opposite.

The second blade 183 of the shaving head 180 has a second slanted rear 197 and a second slanted front 198, a central opening 194, a second angled rear slot 195, and a second angled front slot 196. The distal end of the longitudinal tube 119 has a first lower slanted channel 191 that receives the second slanted rear 197 of the second blade 183, while the proximal end of the nose 121 has a second lower slanted channel 192 that receives the second slanted front 198 of the second blade 183. The proximal guide pin 1100 extends from and through the first and second arms 158, 170 and the second angled rear slot 195 of the second blade 183. The distal guide pin 1101 extends from and through the first and second arms 158, 170 and the second angled front slot 196 of the second blade 183. The second blade 183 also has a groove 199 for shaving and/or receiving vertebral endplate material. While not shown, the first blade 182 has a like groove. The slant of the second angled front slot 196 and the slant of the second angled rear slot 195 are opposite.

FIG. 25 depicts the first and second blades 182, 183 in a retracted position wherein the first and second arms 158, 170 are axially forward of the longitudinal tube 119. FIGS. 26 and 27 depict the first and second blades 182, 183 in an extended position wherein the first and second arms 158, 170 are axially rearward. In this embodiment, when the proximal and distal guide pins 1100, 1101 are caused to axially move through axial translation of the internal control rod (not seen) of the shaft assembly 114, they pull (axial translation towards the proximal end/controller 113) or push (axial translation towards the distal end/shaving head 122) against the angled slots 187, 188, 195, 196 causing the first and second blades to translate up (blade extension) or down (blade retraction). Axial movement is represented by the double-headed arrows.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected. It should be understood that while the use of words such as preferable, preferably, preferred or more preferred utilized in the description above indicate that the feature so described may be more desirable, it nonethe-

What is claimed is:

1. A medical instrument for decorticating a vertebral endplate of a spine comprising:
   a handle;
   a controller operably connected to the handle and including a rotatable control knob with an internally threaded bore, wherein rotation of the handle rotates the rotatable control knob;
   a shaft assembly having a longitudinal tube defining a longitudinal tube proximal end and a longitudinal tube distal end with a control rod disposed therein, the control rod defining a distal control rod end and a proximal control rod, the proximal control rod end having external threading that is received in the internally threaded bore of the rotatable control knob for controlled axial movement of the control rod by the handle;
   a decorticating head disposed at the distal end of the longitudinal tube distal end and defining a decorticating head proximal end and a decorticating head distal end, the decorticating head distal end having a first front angled dovetail slot slanted at a first angle, and a second front angled dovetail slot slanted at a second angle opposite the first angle, the decorticating head proximal end having a first rear angled dovetail slot slanted at a third angle complementary to the first angle of the first front angled dovetail, and a second rear angled dovetail slot slanted at a fourth angle complementary to the second angle of the second front angled dovetail;
   a first blade having a first blade front angled dovetail slanted at a fifth angle being same as the first angle of the first front angled dovetail slot and a first blade rear angled dovetail slanted at a sixth angle being same as the third angle of the first rear angled dovetail slot, the first blade front angled dovetail situated in the first front angled dovetail slot of the decorticating head, and the first blade rear angled dovetail situated in the first rear angled dovetail slot of the decorticating head, whereby the first blade is radially moveable relative to the decorticating head; and
   a second blade having a second blade front angled dovetail slanted at a seventh angle being same as the second angle of the second front angled dovetail slot and a second blade rear angled dovetail slanted at an eighth angle being same as the fourth angle of the second rear angled dovetail slot, the second blade front angled dovetail situated in the second front angled dovetail slot of the decorticating head, and the second blade rear angled dovetail situated in the second rear angled dovetail slot of the decorticating head, wherein the second blade is radially moveable relative to the decorticating head;
   wherein axial force against the first blade via the control rod in a first axial direction effects radially outward movement of the first blade relative to the decorticating head via interaction of the first blade front angled dovetail and the first front angled dovetail slot of the decorticating head, and the first blade rear angled dovetail situated in the first rear angled dovetail slot of the decorticating head, while axial force against the first blade via the control rod in a second axial direction opposite the first axial direction effects radially inward movement of the first blade relative to the decorticating head via interaction of the first blade front angled dovetail and the first front angled dovetail slot of the decorticating head, and the first blade rear dovetail situated in the first rear angled dovetail slot of the decorticating head; and
   wherein axial force against the second blade via the control rod in the first axial direction effects radially outward movement of the second blade relative to the decorticating head via interaction of the second blade front angled dovetail and the second front angled dovetail slot of the decorticating head, and the second blade rear angled dovetail situated in the second rear angled dovetail slot of the decorticating head, while axial force against the second blade via the control rod in the second axial direction opposite the first axial direction effects radially inward movement of the second blade relative to the decorticating head via interaction of the second blade front angled dovetail and the second front angled dovetail slot of the decorticating head, and the second blade rear angled dovetail situated in the second rear angled dovetail slot of the decorticating head.

2. The medical instrument of claim 1, wherein the first axial direction comprises compression against a front of the first blade and a front of the second blade.

3. The medical instrument of claim 2, wherein the first blade has a first angled cutout and a second angled cutout, and the second blade has a third angled cutout and a fourth angled cutout.

4. The medical instrument of claim 3, wherein the first angled cutout of the first blade is situated proximate to the decorticating head distal end, the second angled cutout of the first blade is proximate to the decorticating head proximal end, the third angled cutout of the second blade is situated proximate to the decorticating head distal end, and the fourth angled cutout of the second blade is proximate to the decorticating head proximal end.

5. The medical instrument of claim 4, wherein the first and second angled cutouts of the first blade are situated skewed relative to each other, and the third and fourth angled cutouts of the second blade are situated skewed relative to each other.

* * * * *